United States Patent [19]

Vaughan

[11] Patent Number: 4,695,025
[45] Date of Patent: Sep. 22, 1987

[54] HANGER ASSEMBLY

[76] Inventor: Thomas L. Vaughan, 27272 Cool Water Ranch Rd., Valley Center, Calif. 92082

[21] Appl. No.: 793,963

[22] Filed: Nov. 1, 1985

[51] Int. Cl.[4] .............................................. E04G 3/00
[52] U.S. Cl. ...................................... 248/293; 403/93
[58] Field of Search ............... 248/122, 121, 293, 159, 248/439, 166, 318; 403/157, 65, 93, 98; 211/205, 117

[56] References Cited

U.S. PATENT DOCUMENTS

| 530,726 | 12/1894 | Scott et al. | 403/93 X |
| 737,951 | 9/1903 | McEachern | 403/93 X |
| 1,560,279 | 11/1925 | Marks | 248/159 X |
| 2,420,267 | 5/1947 | Sefried | 403/157 X |
| 3,318,457 | 5/1967 | Krasnoff | 248/125 X |
| 4,289,244 | 9/1981 | Frankhouser | 248/318 X |
| 4,332,378 | 6/1982 | Pryor | 248/125 X |

FOREIGN PATENT DOCUMENTS 355468 6/1905 France .................................. 403/93

Primary Examiner—J. Franklin Foss
Attorney, Agent, or Firm—Knobbe, Martens, Olson & Bear

[57] ABSTRACT

A hanger assembly is disclosed having pivotable arms locking in an operational position, and unlocking to be movable to a storage position. To enhance portability of the assembly, the connection between the assembly and a supporting pole is easily attachable and detachable. The hanger assembly is locked into operation by means of a biased mating engagement between a hanger arm and a cross-arm. Unlocking into a storage position is easily accomplishable by application of force against the biasing force to remove the arms from mating engagement, and then rotating the arms about the pivot point. Hanging of equipment is provided by means disposed on the hanger arm.

26 Claims, 5 Drawing Figures

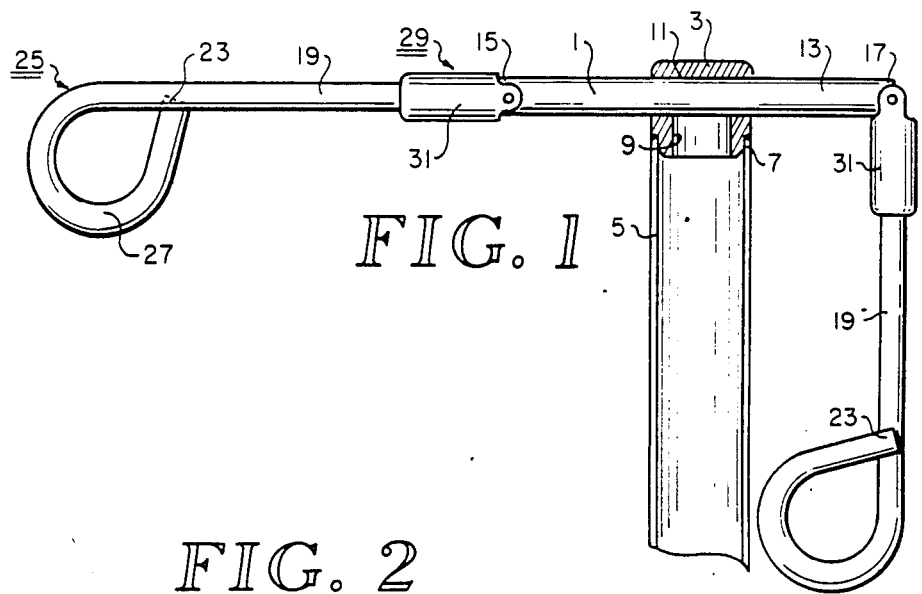
FIG. 1
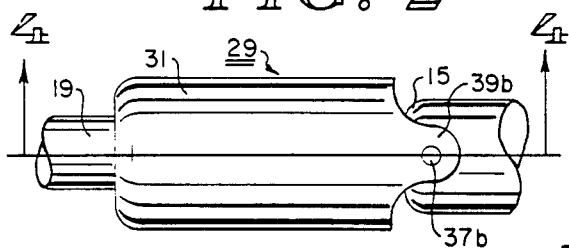
FIG. 2
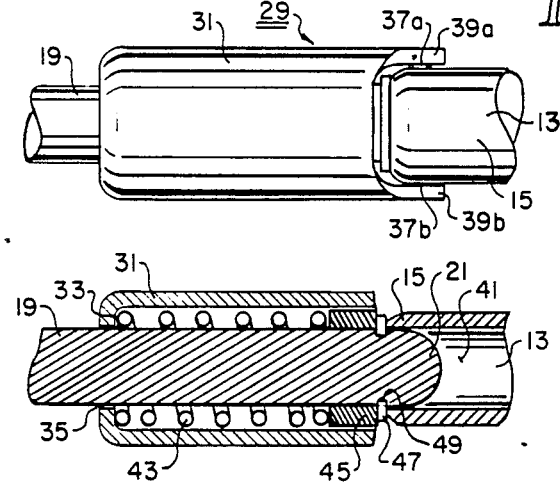
FIG. 3
FIG. 5
FIG. 4
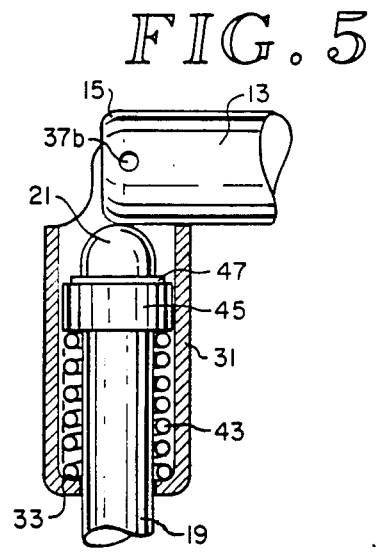

HANGER ASSEMBLY

BACKGROUND OF THE INVENTION

1. Field of the Invention

This invention pertains to the field of medical care products. More particularly, it pertains to medical hardward and specifically, a hanger assembly for an upright pole upon which is hung various medical devices such as intravenous bags, blood monitors, nurse identification devices and blood pressure equipment.

2. Description of the Prior Art

Inpatient medical care has been traditionally confined to the hospital. Hospitals have large storage areas and thus there was no need for medical hardware to be collapsible and it was stored in fully extended geometry. All that has since changed. With higher hospital care costs, hospital fixed expenses have been forced to be minimized and storage area has been converted to bed space. This requires hospital hardware to be stored in smaller spaces and extreme hardship has been encountered in that fully extended hardware is not only difficult to store in a confined area but substantial damage is caused to the hardware under these conditions.

In addition, there has been a surge in the development of small, economic treatment facilities in an effort to minimize capital expenses. These small treatment facilities have little storage area and medical hardware is required to be capable of confined storage.

Further, the median age of the united State population is on the increase. This has resulted in more elderly people and concomitantly a greater need for medical care. The government has been instrumental in attempting to decrease hospital and medical care coverage and this has resulted in private efforts to conduct medical treatment in the home. Home treatment, such as administration of intravenous solutions and extended convalescent care necessitates the transport of medical hardward via automobile and these factors have fostered the development of collapsible medical hardware.

SUMMARY OF THE INVENTION

This invention comprises a hanger assembly for an upright support hardware pole that is foldable to a small configuration for ease in transport and storage. The traditional long, heavy hanger arm has been changed to an articulated radial arm capable of being locked into horizontal support position and unlocked and folded into a small geometry storage condition. The folded hanger assembly allows the visiting nurse or home owner to easily load and transport a plurality of these devices in a passenger vehicle where such would not be the case with the traditional fully extended hanger assembly.

This invention comprises a plug for attachment to the top or upper portion of the support pole, a cross-arm extending horizontally therefrom, a hanger arm pivotally connected to the cross-arm and containing means for hanging medical equipment therefrom and means for locking the cross-arm and hanger arm into mutual horizontal axial alignment during use with medical equipment and thereafter unlocking the hanger arm to permit it to be folded into a storage position adjacent or parallel to the support pole.

Accordingly, the main object of this invention is a hanger assembly for an upright medical equipment support pole that is foldable to a small geometry for ease in storing and transportation. Other objects include a hanger assembly that contains a convenient means of hanging an intravenous bag therefrom; a hanger assembly that is easily, quickly and conveniently foldable to a storage configuration and unfoldable into a working configuration merely by pulling the hanger arm out of axially aligned receipt in a bore formed in the end of the cross-arm; a hanger assembly that is retrofittable to virtually every medical equipment support pole in existence and a hanger assembly that is of simple construction, of relatively few parts, in a rugged configuration for ready acceptance by the medical trade.

These and other objects of the invention will become more apparent upon a close reading of the Description of the Preferred Embodiment taken together with the drawings attached hereto. While only one embodiment of the hanger assembly will be described and shown, other equivalent constructions are fully contemplated within the spirit and scope of this invention.

DESCRIPTION OF THE DRAWINGS

FIG. 1 is a side plan view, partially in section, of one embodiment of the hanger assembly of this invention shown mounted to a typical medical equipment support pole.

FIG. 2 is a side plan view of the exterior of the sleeve that comprises part of the locking mechanism.

FIG. 3 is the same view as in FIG. 2 except that the sleeve and the associated arm ends are rotated through 90 degrees.

FIG. 4 is a sectional side view of the embodiment shown in FIG. 2 taken along lines 4—therein.

FIG. 5 is a partially sectional view of the same embodiment shown in FIG. 4 except that the arms are unlocked and rotated into storage position.

DESCRIPTION OF THE PREFERRED EMBODIMENT

In FIG. 1 is shown one embodiment of the hanger assembly 1 of this invention. Shown is a plug 3 for attachment to the top end of a typical hollow aluminum or stainless steel medical equipment support pole 5. Plug 3 includes a male portion 7, for insertion into hollow pole 5 or for direct attachment should pole 5 be of the solid variety. Male portion 7 is attached to pole 5 by any convenient means including welding, glueing or threading as is known in the art. A female portion 9 extends up from male portion 7 and includes a cross-bore 11 formed therethrough.

A cross-arm 13 is received in cross-bore 11 and, as shown, comprises a solid rod extending completely therethrough to terminate at a pair of opposed ends 15 and 17, both spaced apart from pole 5. Cross-arm 13, however, for other reasons, can merely extend horizontally in one direction only so that terminal end 15 would be spaced apart from pole 5 and terminal end 17 housed or carried in cross-bore 11. This modification is fully contemplated within the scope of this invention.

A hanger arm 19, having first and second ends 21 and 23 respectively is shown, wherein first end 21 is adapted to contact cross-arm end 15 for locked axial alignment and unlocked storage configuration as explained hereinafter. Where cross-arm 13 passes completely through cross-bore 11, a second hanger arm 19 will be connected to end 17 as shown in FIG. 1. For clarity purposes, only one hanger arm assembly will be described, all others being of the same or similar geometry.

On hanger arm 19 is formed means 25 for hanging medical equipment therefrom. As shown, means 25 comprises a loop 27 bent or formed in hanger arm 19 wherein the terminal end 23 extends in an upwardly direction, when said hanger arm 19 is positioned in its horizontal, medical equipment support geometry. Further, hanger arm second end 23 is spaced slightly apart from the center straight portion of hanger arm 19 so that medical equipment, such as an Intravenous bag, having an end support tab containing an aperture therein, may be conveniently hung from loop 27 by placing the hanging aperture over second end 23 and rotating the bag so that it hangs vertically downward from loop 27.

Positioned adjacent hanger arm first end 21 is means 29 for locking cross-arm 13 and hanger arm 19 into mutual axial alignment, as shown on the left side of FIG. 1, and thereafter unlocking to permit hanger arm 19 to be swung downward into storage positon adjacent or parallel to pole 5 as is shown on the right side of FIG. 1.

Means 29 generally comprises a sleeve 31 slidingly disposed on one of said arms, either cross-arm 13 or hanger arm 19 and pivotally connected to the other of said arms, either hanger arm 19 or cross-arm 13, across the contact point between cross-arm end 15 and hanger arm first end 21. As shown in FIGS. 2 through 5, sleeve 31 is slidingly disposed over hanger arm 19 and has an inwardly turned end terminating in an aperture 35 through which hanger arm 19 may move in reciprocal motion.

Sleeve 31 is hingedly connected to cross-arm end 15 by a pair of axially aligned short hinge-pins 37a and 37b that are received in a pair of mutually opposed ears 39a and 39b extending from the opposite end of sleeve 31. An axial bore 41 is formed in cross-arm end 15 and spans the distance between hinge-pins 37a and 37b and is of a size and shape adapted to receive hanger arm first end 21 therein. A coil spring 43 is disposed over hanger arm 19 and compressed between inwardly tapered end or stop 33 and a second stop or collar 45 affixed to hanger arm 19 and secured thereto by a snap ring 47 mounted in a groove 49 formed circumferentially thereabout. Spring 43 urges hanger arm 19 and hanger arm first end 21 into receipt within bore 41 to lock cross-arm 13 and hanger arm 19 in axial alignment. Penetration of hanger arm first end 21 into bore 41 is limited by snap ring 45 coming into abutment with cross-arm end 15, see FIG. 4. As shown in FIG. 5, hanger arm 19 may be unlocked from axial alignment with cross-arm 13 by pulling outward on hanger arm 19 to overcome the compression bias of coil spring 43 and withdraw hanger arm first end 21 from bore 41. Thereafter, hanger arm 19 and sleeve 31 may be rotated through an angle such as 90 degrees to place them parallel to pole 5 for storage and transfer purposes.

What is claimed is:

1. A hanger assembly for an upright equipment pole, said assembly comprising:
   (a) means for attaching the hanger assembly to the equipment pole;
   (b) a cross-arm extending from said attaching means and terminating at a terminal end spaced apart from the pole;
   (c) a hanger arm having first and second ends, said first end mating with the terminal end of said cross-arm in at least one configuration of the hanger assembly, said hanger arm comprising means for hanging equipment therefrom; and
   (d) means proximate to said first end for locking said cross-arm and said hanger arm into an operational configuration such that equipment may be hung therefrom, and thereafter unlocking said arms to permit said hanger arm to be swung into a storage configuration.

2. The hanger assembly of claim 1 wherein the equipment pole includes a hollow top end and wherein said attaching means comprises a plug which includes a male portion, for insertion into the hollow top end.

3. The hanger assembly of claim 1 wherein said attaching means comprises a plug which includes a male portion for attachment to the equipment pole.

4. The hanger assembly of claim 1 wherein said cross-arm extends completely through said attaching means.

5. The hanger assembly of claim 1 wherein said means for hanging equipment comprises a loop formed in said hanger arm terminating at said second arm end, and extending in an upwardly direction when the configuration of the hanger assembly is such that said hanger arm is locked with said cross-arm.

6. The hanger assembly of claim 1 wherein said means for locking and unlocking said cross-arm comprises:
   (a) a sleeve slidingly disposed on one of said arms and pivotally connected to the other of said arms said pivot connection defining an arc between the respective hanger arm and the terminal end; and
   (b) means in said sleeve biasing the arms disposed within said sleeve toward mutual engagement.

7. The hanger assembly of claim 6 wherein said terminal end of said cross-arm defines an axial bore wherein said hanger arm first end comprises a structure that may be slideably received in mating engagement within said bore, and wherein said biasing means comprises a coil spring disposed over a portion of said hanger arm.

8. The hanger assembly of claim 7 wherein said hanger arm defines an annular groove proximate to said first end, and said second stop comprises an annular clip mounted about said annular groove, and said second stop further comprises a collar adjacent to said spring on one side and adjacent to said clip on the other, said clip acting to limit entry of said hanger arm first end into said bore by abutment of said clip against the portion of said cross-arm surrounding said bore.

9. A hanger assembly for an upright equipment support pole, comprising:
   (a) means for attaching the hanger assembly to the equipment pole;
   (b) a cross-arm extending completely through said attaching means, said cross arm terminating at a pair of opposed terminal ends, both spaced apart from the pole;
   (c) two hanger arms having first and second ends, each of said first ends mating with the respective cross-arm terminal end in at least one configuration of the hanger assembly, each of said hanger arms comprising means for hanging equipment therefrom; and
   (d) means proximate to each of said first ends for locking said cross-arm and said hanger arm respectively into an operational configuration of mutual axial alignment such that equipment may be hung therefrom and for thereafter unlocking said respective cross-arm and said hanger arm to permit said hanger arm to be swung into storage configuration parallel the equipment pole.

10. The hanger assembly of claim 9 wherein each of said terminal ends of said cross-arm define an axial bore, wherein said hanger arm first end comprises a structure that may be slideably received within said bore, and wherein said biasing means comprises a coil spring disposed over a portion of said hanger arm.

11. The hanger assembly of claim 10 wherein said hanger arm defines an annular groove proximate to said first end, and said second stop comprises an annular clip mounted about said annular groove, and said second stop further comprises a collar adjacent to said spring on one side and adjacent to said clip on the other, said clip acting to limit entry of said hanger arm first end into said bore by abutment of said clip against the portion of said cross-arm surrounding said bore.

12. The hanger assembly of claim 9 wherein the equipment pole includes a hollow top end and wherein said attaching means comprises a plug which includes a male portion, for insertion into the hollow top end.

13. The hanger assembly of claim 9 wherein said attaching means comprises a plug, which plug includes a male portion for attachment to the support pole and a female portion for receipt of said cross-arm.

14. The hanger assembly of claim 9 wherein said means for locking and unlocking said cross-arm comprises:
(a) a sleeve slidingly disposed on one of said arms and pivotally connected to the other said arm, said pivotal connection defining an arc between the respective hanger arm and the terminal end; and
(b) means in said sleeve biasing the arms toward mutual engagement.

15. The hanger assembly of claim 1 wherein said attaching means comprises means for removably detaching and re-attaching said hanger assembly from the equipment pole.

16. The hanger assembly of claim 1 wherein said cross-arm extends in a direction orthogonal to the equipment pole.

17. The hanger assembly of claim 1 wherein the operational configuration corresponds to the position wherein said hanger arm is in axial alignment with said cross-arm.

18. The hanger assembly of claim 7 wherein a first stop is formed in said sleeve, wherein a second stop is affixed to said hanger arm, and wherein said spring is compressed between said first and said second stops.

19. The hanger assembly of claim 7 wherein said first end and said cross-arm ae biased into mutual contact throughout the arc defined by said pivotal connection between the sleeve and the cross-arm, and wherein said first end comprises a dome shape and wherein the terminal end defines a curve about said bore so that said contact point between said first end and said cross-arm terminal end is slideable throughout said arc from operational configuration to the storage configuration at which storage configuration the shape of the terminal end at said contact point with said cross-arm terminal end provides resistance to further rotation in either direction.

20. The hanger assembly of claim 1 further comprising:
a plurality of cross-arms extending from said attaching means and each terminating at a terminal end spaced apart from the pole; and
a plurality of hanger arms, each of said hanger arms having first and second ends, said first ends mating with the terminal end of said cross-arm in at least one configuration of the hanger assembly, each said hanger arm comprising means for hanging equipment therefrom.

21. The hanger assembly of claim 18 wherein said second stop limits entry of said hanger arm first end into said axial bore by abutment of said clip against a portion of said end of said cross-arm.

22. The hanger assembly of claim 10 wherein said first end and said cross-arm are biased into mutual contact throughout the arc defined by said pivotal connection between the sleeve and the cross-arm, and wherein said first end comprises a dome shape and wherein the terminal end defines a curve about said bore so that said contact point between said first end and said cross-arm terminal end is slideable throughout said arc from operational configuration to the storage configuration, at which storage configuration the shape of the terminal end at said contact point with said cross-arm terminal end provides resistance to further rotation in either direction.

23. The hanger assembly of claim 10 wherein a first stop is formed in said sleeve, wherein a second stop is affixed to said hanger arm, and wherein said spring is compressed between said first and second stops.

24. The hanger assembly of claim 1 wherein the cross-arm comprises a tubular structure defining an inner axial bore extendng throughout said cross-arm.

25. The hanger assembly of claim 9 wherein the cross-arm comprises a tubular structure defining an inner axial bore extending throughout said cross-arm.

26. A hanger assembly for an upright equipment pole having a hollow top end, said assembly comprising:
(a) means for attaching the hanger assembly to the equipment pole, said attaching means including a plug for removable insertion into the top end of the equipment pole;
(b) a cross-arm extending completely through said plug, said cross-arm terminating at a pair of opposed terminal ends, both said terminal ends spaced apart from the pole, each said terminal end defining an axial bore and further defining a curve about said axial bore;
(c) two hanger arms having first and second ends, each of said first ends comprising a dome shape and further comprising a first stop proximate to said dome shape, each of said hanger arms also comprising means for hanging equipement therefrom;
(d) a sleeve slidingly disposed on each of said hanger arms and pivotally connected to the respective cross-arm, said pivot connection defining an arc between the hanger arm and the respective cross-arm terminal end, said arc including at least two configurations, including a storage configuration and an operational configuration;
(e) means in the sleeve for biasing the hanger arm and respective cross-arm toward mutual engagement, said biasing means including a coil spring disposed within the sleeve and annularly abutting a portion of the hanger arm;
(f) said operational configuration including a mating of the dome shaped hanger arm end with the axial bore, such that the biasing means provide force to maintain said mating and such that the first stop on the hanger arm abuts the respective terminal end to prevent further insertion; and
(g) said storage configuration including a slideable contact between the dome shape and the curve about the axial bore.

* * * * *